United States Patent [19]

Kern et al.

[11] Patent Number: 4,918,108

[45] Date of Patent: Apr. 17, 1990

[54] METHOD OF IMPROVING THE ABSORPTION OF INJECTED ANTIBACTERIAL SUBSTANCES

[75] Inventors: Otto Kern; Franz Wilhelm; Ernst Salamon, all of Ingelheim am Rhein, Fed. Rep. of Germany

[73] Assignee: Boehringer Ingelheim Vetmedica GmbH, Ingelheim am Rhein, Fed. Rep. of Germany

[21] Appl. No.: 68,036

[22] Filed: Jun. 29, 1987

Related U.S. Application Data

[63] Continuation-in-part of Ser. No. 825,785, Feb. 3, 1986, Pat. No. 4,705,803, which is a continuation of Ser. No. 471,299, Mar. 2, 1983, abandoned.

[30] Foreign Application Priority Data

Mar. 16, 1982 [DE] Fed. Rep. of Germany ....... 3209429

[51] Int. Cl.$^4$ ................. A61K 31/165; A61K 31/135; A61K 31/335
[52] U.S. Cl. ................................. 514/621; 514/450; 514/643
[58] Field of Search ............... 514/450, 653, 450, 653, 514/621

[56] References Cited

PUBLICATIONS

Chem. Abst. 97:11868t.
Chem. Abst. 95:73109p.
Goodman et al., *The Pharmacological Basis of Therapeutics*, 6th Ed., (1980), pp. 1185–86.

*Primary Examiner*—Douglas W. Robinson
*Assistant Examiner*—Russell Travers
*Attorney, Agent, or Firm*—Walter G. Weissenberger

[57] ABSTRACT

An antibacterial substance which does not have optimum absorbability and is administered parentally into tissue, is administered to a host in conjunction with a benzylamine derivative of the formula

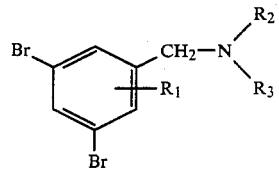

wherein
  $R_1$ is hydroxyl in the 2- or 4-position or amino in the 2-position;
  $R_2$ is hydrogen or alkyl of 1 to 3 carbon atoms; and
  $R_3$ is cyclohexyl optionally substituted by hydroxyl;
or a non-toxic, pharmacologically acceptable acid addition salt thereof, to improve the absorption of the parenterally administered antibacterial substance.

1 Claim, No Drawings

METHOD OF IMPROVING THE ABSORPTION OF INJECTED ANTIBACTERIAL SUBSTANCES

This is a continuation-in-part of copending application Ser. No. 825,785, filed February 3, 1986, now U.S. Pat. No. 4,705,803; which in turn is a continuation of application Ser. No. 471,299, filed March 2, 1983, now abandoned.

FIELD OF INVENTION

This invention relates to a method of improving the absorption of injected antibacterial substances. More specifically, this invention relates to the use of benzylamine derivatives in combination with injected antibacterial substances to improve the absorption of said antibacterial substances after injection.

BACKGROUND OF THE INVENTION

It is known from the literature that benzylamine derivatives are useful as bronchosecretolytics in human and veterinary medicine. The best known examples of these benzylamine derivatives are N-(2-amino-3,5-dibromobenzyl)-N-methyl-cyclohexylamine hydrochloride (generic name: bromhexine) and N-(2-amino-3,5-dibromobenzyl)-trans-4-hydroxycyclohexylamine hydrochloride (generic name: ambroxol). These compounds produce a significant increase in the quantity of secretion, but it has been found that the viscosity of the secretion decreases and the concentration of solids in the fluid of the respiratory tract and their specific weight are reduced, which characterizes the benzylamine derivatives as secretolytics.

In addition, it is known from the literature that when the above-mentioned benzylamine derivatives are administered perorally together with an antibiotic, particularly oxytetracycline and erythromycin, or with a sulfonamide such as sulfadiazine, there is an increase in the infiltration of these substances into the bronchial secretion. The same also applies to the body's own immunoglobulins, that is, immunoglobulins which have not been administered. However, this increase in the concentration of the contents of bronchial secretion is not caused by any increased absorption from the intestines induced by the above-mentioned benzylamine derivatives or by any delay in excretion through the kidneys, since there is no detectable increase in blood level values after oral or intravenous administration.

OBJECTS OF THE INVENTION

It is an object of the invention to provide a method of improving the absorption of injected antibacterial substances or combinations.

It is also an object of this invention to provide a combination of an antibacterial substance or combinations and a benzylamine derivate.

It is a further object of this invention to provide a method of improving the absorption of an injected antibacterial substance or combination by admixing said substance with an effective amount of a benzylamine derivative of the formula

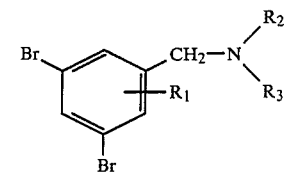

wherein
$R_1$ is hydroxyl in the 2- or 4-position or amino in the 2-position;
$R_2$ is hydrogen or alkyl of 1 to 3 carbon atoms; and
$R_3$ is cyclohexyl hydroxy-cyclohexyl;
or a non-toxic, pharmacologically acceptable acid addition salt thereof.

These and other objects of the invention will become apparent as the description thereof proceeds.

DETAILED DESCRIPTION OF THE INVENTION

We have discovered that when a benzylamine derivative of the formula I above or a non-toxic, pharmacologically acceptable acid addition salt thereof is administered parenterally, the absorption of an antibacterial substance or combination which has been administered parenterally into the tissues and which, on its own, does not have optimum absorbability, is speeded up. Thus, according to the invention, as a result of the higher blood levels with the same dosage of the antibacterial substance, or combination better and safer therapeutic results are obtained or—if higher blood levels are not wanted—the quantity administered can be reduced by comparison with the quantity required when the substance in question is administered by itself, and consequently a significant saving is achieved. Moreover, the problem of residues is reduced since the injection site for the antibacterial substances and combinations in question is usually the tissue, which retains measurable residues of these substances longest.

Therefore, the present invention relates to the novel use of the benzylamine derivatives of the formula I and non-toxic, pharmacologically acceptable acid addition salts thereof, preferably in veterinary medicine, for increasing the absorption of antibacterial substances or combinations which have been administered parenterally into the tissue and are not readily absorbed, preferably by parenteral administration of the benzylamine derivatives at the same time.

The preferred benzylamine derivatives of the formula I are, however, those wherein $R_2$ and $R_3$, together with the nitrogen atom to which they are attached, form an N-methylcyclohexylamino, N-ethyl-cyclohexylamino, trans-4-hydroxycyclohexylamino, or cis-3-hydroxy-cyclohexylamino group. A particularly preferred benzylamine derivative of the formula I is N-(3,5-dibromo-2-hydroxybenzyl)-trans-4-hydroxy-cyclohexylamine or a non-toxic, pharmacologically acceptable acid addition salt thereof, especially the hydrochloride.

Examples of antibacterial substances used according to the invention, optionally in the form of esters or salts thereof, include the following: antibiotics of the tetracycline group, such as oxytetracycline, oxytetracycline hydrochloride, rolitetracycline or doxycycline; difficultly soluble antibiotics of the β-lactam group, such as procaine penicillin, benethamine penicillin, benzathine penicillin, the benzathine salts of oxacillin, cloxacillin, or ampicillin, and of the cephalosporins; erythromycin and derivatives thereof, such as 9-deoxy-11-deoxy-9,11-{imino-[2-(2-methoxyethoxy)-ethylidene]-oxy}-(9F)-erythromycin, erythromycin lactobionate, erythromycin ethylsuccinate or erythromycin glucoheptonate; spiramycin or spiramycin adipate; tylosin or tylosin tartrate; oleandomycin; chloramphenicol or chloramphenicol succinate; thiamphenicol or thiamphenicol glycinate; sulfonamides or sodium salts thereof, such as sulfadiazine, sulfadoxine, sulfamethoxazole, sulfadimethoxine, sulfadimidine or sulfathiazole; a sulfonamide together with an agonist such as trimethoprim, for example, the sulfadimidine/sulfathiazole/trimethoprim combination, or the sodium salts thereof; and, optionally, the delayed-release forms thereof.

The invention further relates to the novel combinations which are suitable for parenteral administration into the tissue, containing a benzylamine derivative of the formula I and an antibacterial substance or combination which, by itself, does not have optimum absorbability, together with one or more conventional inert diluents or carriers, preferably those forms which are suitable for intramuscular administration. The preferred combinations are those containing (1) a benzylamine derivative of the formula I wherein $R_1$ is hydroxyl and $R_2$ and $R_3$, together with the nitrogen atom to which they are attached, have the meanings defined above, preferably N-ethylcyclohexylamino, trans-4-hydroxycyclohexylamino, or cis-3-hydroxy-cyclohexylamino, and especially wherein $R_1$ is hydroxyl in the 2-position, and $R_2$ and $R_3$, together with the nitrogen atom to which they are attached, are trans-4-hydroxy-cyclohexylamino, and (2) one of the above-mentioned antibacterial substances or combinations.

Particularly preferred embodiments of the invention are (A) the combination of (1) N-(2-amino-3,5-dibromobenzyl)-N-methyl-cyclohexylamine or a non-toxic, pharmacologically acceptable acid addition salt thereof, and (2) a delayed-release oxytetracycline preparation, a delayed-release oxytetracycline hydrochloride preparation, rolitetracycline or docycycline;

(i) a difficultly soluble antibiotic of the β-lactam group, such as procaine penicillin, benethamine penicillin, benzathine penicillin or a benzathine salt of oxacillin, cloxacillin, ampicillin or a cephalosporin;

(ii) erythromycin or a derivative thereof, such as 9-deoxy-11-deoxy-9,11-{imino-[2-(2-methoxyethoxy)-ethylidene]-oxy}-(9F)-ethromycin, erythromycin lactobionate, erythromycin ethylsuccinate, erythromycin glucoheptonate; spiramycin, spiramycin adipate; tylosin, tylosin tartrate; oleandomycin; thiamphenicol or thiamphenicol glycinate; or (iii) a sulfonamide or a sodium salt thereof, such as sulfadiazine, sulfadoxine, sulfamethoxazole, sulfadimethoxine, sulfadimidine, or sulfathiazole, or a sulfonamide combination with an agonist such as trimethoprim, for example, the sulfadimidine/sulfathiazole/trimethoprim combination; or (B) the combination of (1) N-(2-amino-3,5-dibromobenzyl)-trans-4-hydroxy-cyclohexylamine or a non-toxic, pharmacologically acceptable acid addition salt thereof, and (2)

(i) an antibiotic of the tetracycline group, such as oxytetracycline, oxytetracycline hydrochloride, rolitetracycline or doxycycline;

(ii) a difficultly soluble antibiotic of the β-lactam group, such as procaine penicillin, benethamine penicillin, benzathine penicillin or a benzathine salt of oxacillin, cloxacillin, ampicillin or a cephalosporin;

(iii) erythromycin or one of the derivatives thereof, such as 9-deoxy-11-deoxy-9,11-{imino-[2-(2-methoxyethoxy)-ethylidene]-oxy}-(9F)-erythromycin, erythromycin lactobionate, erythromycin ethylsuccinate, erythromycin glucoheptonate; spiramycin, spiramycin adipate; tylosin, tylosin tartrate; oleandomycin; chloramphenicol, chloramphenicol succinate; thiamphenicol or thiamphenicol glycinate; or (iv) a sulfonamide or a sodium salt thereof, such as sulfadiazine, sulfadoxine, sulfamethoxazole, sulfadimethoxine, sulfadimidine or sulfathiazole, or a combination of a sulfonamide with an agonist such as trimethoprim, for example, the sulfadimidine/sulfathiazole/trimethoprim combination, or, optionally, a corresponding delayed-release form.

The following combinations are, however, particularly preferred:

(a) Combinations of (1) N-(2-amino-3,5-dibromo-benzyl)-N-methyl-cyclohexylamine or a non-toxic, pharmacologically acceptable acid addition salt thereof, or N-(3,5-dibromo-2-hydroxy-benzyl)-trans-4-hydroxy-cyclohexylamine or a non-toxic, pharmacologically acceptable acid addition salt thereof with (2) erythromycin, erythromycin lactobionate, erythromycin ethylsuccinate, erythromycin glucoheptonate, 9-deoxy-11-deoxy-9,11-{imino-[2-(2-methoxyethoxy)-ethylidene]-oxy}-(9F)-erythromycin, tylosin, tylosin tartrate, spiramycin, spiramycin adipate, oleandomycin, benethamine penicillin, benzathine penicillin, ampicillin, oxacillin, cloxacillin, rolitetracycline, doxycycline, or a salt thereof; or a sulfonamide or a salt thereof, optionally in combination with trimethoprim; and (b) Combinations of (1) N-(3,5-dibromo-2-hydroxy-benzyl)-trans-4-hydroxy-cyclohexylamine or a non-toxic, pharmacologically acceptable acid addition salt thereof with oxytetracycline or a salt thereof, chloramphenicol, chloramphenicol succinate, thiamphenicol or thiamphenicol glycinate.

To demonstrate the efficacy of the invention, the absorption-promoting effect of the following benzylamine derivatives:

A=N-(2-amino-3,5-dibromo-benzyl)-N-methyl-cyclohexylamine hydrochloride;

B=N-(2-amino-3,5-dibromo-benzyl)-trans-4-hydroxy-cyclohexylamine hydrochloride, and C=N-(3,5-dibromo-2-hydroxy-benzyl)-trans-4-hydroxycyclohexylamine hydrochloride, was tested in the following manner:

Cattle, pigs, and sheep (with the same ten animals per group) were treated once with only the antibacterial substance or combination in question and once with the combination of the benzylamine derivative together with the same antibacterial substance or combination, administered by the intramuscular route. The two treatments were given at an interval of eight days to ensure that the substance or substances administered in the first treatment had been totally eliminated. The order of treatment varied, that is, in some cases the antibacterial substance or combination (control) was administered first and in some cases the combination including the benzylamine derivative was administered first (test group). In some cases the tests were carried out as "cross-over" tests, that is, on the first occasion five animals were given the antibacterial substance or combination while five animals were given the combination including the benzylamine derivative. When the test was repeated eight days later, the treatments were reversed.

Blood samples were taken during the day at one and two hour intervals and after 24 hours, and in some cases after 32 hours as well, and in two cases (delayed-release preparations) after 48 and 72 hours also. The levels of antibiotics or sulfonamide in the blood serum were determined using conventional microbiological methods with test pathogens specific to each substance.

In each case, the areas under the blood level curves obtained were compared, as an overall measurement of antibacterial activity. This comparison showed increases in blood level for the combination of benzylamine derivatives with the antibacterial substance or combination in question, compared with the control group in question, as is shown in the following table:

TABLE 1

| Antibacterial Substance or Combination | (Dosage: mg/kg of body weight) | Benzylamine Derivative (Dosage: mg/kg) | | Type of Animal | Increase in Blood Level (in %, compared with control) |
|---|---|---|---|---|---|
| Erythromycin | 10 | A | 0.3 i.m. | cattle | 16.1 |
| | 10 | C | 0.6 i.m. | cattle | 21.4 |
| | 10 | A | 0.6 i.m. | pig | 59.1 |
| | 10 | A | 1.2 i.m. | pig | 31.4 |
| Erythromycin derivative | 10 | A | 1.2 i.m. | pig | 15.3 |
| | 10 | C | 1.2 i.m. | pig | 45.4 |
| Oxytetracycline hydrochloride | 10 | C | 0.6 i.m. | cattle | 16.3 |
| Delayed-release oxytetracycline preparation* | 20 | A | 0.6 i.m. | pig | 109.5 |
| | 20 | C | 1.2 i.m. | pig | 80.0 |
| Tylosin | 15 | A | 0.3 i.m. | cattle | 33.0 |
| | 15 | C | 0.6 i.m. | cattle | 23.5 |
| Tylosin | 10 | A | 0.6 i.m. | pig | 19.3 |
| | 10 | A | 1.2 i.m. | pig | 30.3 |
| | 10 | C | 0.6 i.m. | pig | 30.5 |
| | 10 | C | 1.2 i.m. | pig | 26.1 |
| Sulfadimidine/— | 24 | A | 0.6 i.m. | pig | 29.6 |
| Sulfathiazole/— | 24 | A | 1.2 i.m. | pig | 25.1 |
| Trimethoprim | 24 | C | 0.6 i.m. | pig | 29.9 |
| Combination (10:10:4) | 24 | C | 1.2 i.m. | pig | 20.3 |

*Blood level monitored for 72 hours; after 48 hours it is 0.13 μg/ml for the control but 0.35 μg/ml for the test group; after 72 hours, it is 0.00 μg/ml for the control but still 0.19 μg/ml for the test group.

The benzylamine derivatives of the formula I and their non-toxic, pharmacologically acceptable acid addition salts are well tolerated. For example, the acute toxicity ($LD_{50}$) in the mouse is >400 mg/kg i.p. for Compound A,
268 mg/kg i.p. for Compound B, and
>800 mg/kg i.p. for Compound C.

In view of the above-mentioned biological characteristics, the benzylamine derivatives of the formula I and their non-toxic, pharmacologically acceptable acid addition salts are, as mentioned above, suitable for improving the absorption of antibacterial substances or combinations administered parenterally into the tissue, and thus help to improve and guarantee the success of the therapy. The dosage is advantageously above 0.1 mg/kg, preferably between 0.2 and 2.0 mg/kg, while in solutions the upper limit is set by the solubility of the particular benzylamine derivative which is used. For example, in water, Compounds A to C have the following maximum solubilities:

| Compound | Maximum Solubility |
|---|---|
| A | 0.2 to 5.0 mg/cm³ |
| B | 16.6 mg/cm³ |
| C | 0.1 to 1.0 mg/cm³ | dependent upon the pH in the acid range. Obviously, higher concentrations can be achieved in oily carriers, dependent upon the solubility in oil of the benzylamine derivative and also upon whether the benzylamine derivative is suspended in suitable carriers in which it is insoluble or not sufficiently soluble.

Moreover, the benzylamine derivative is preferably administered simultaneously with a therapeutic dose of the antibacterial substance or combination which is to be used. Examples of individual doses include the following:

TABLE 2

| Active Substance | Dose |
|---|---|
| oxytetracycline | 5 to 30 mg/kg |
| rolitetracycline | 15 to 50 mg/kg |
| doxycycline | 2 to 5 mg/kg |
| erythromycin | 5 to 20 mg/kg |
| 9-deoxy-11-deoxy-9,11-{imino-[2-(2-methoxyethoxy)-ethylidene]-oxy}-(9F)-erythromycin | 5 to 20 mg/kg |
| spiramycin | 10 to 50 mg/kg |
| tylosin | 5 to 20 mg/kg |
| chloramphenicol | 10 to 50 mg/kg |
| thiamphenicol | 10 to 50 mg/kg |
| sulfadiazine | 15 to 50 mg/kg |
| sulfadiazine/sulfathiazole/-trimethoprim | 15 to 30 mg/kg |
| sulfadoxin/trimethoprim | 15 to 30 mg/kg |
| procaine penicillin | 2,000 to 20,000 I.U./kg |
| benzathine penicillin | 6,000 to 25,000 I.U./kg |
| ampicillin | 2 to 15 mg/kg |
| oxacillin | 5 to 15 mg/kg |
| cloxacillin | 5 to 15 mg/kg |
| oxytetracycline hydrochloride | 2 to 25 mg/kg |

Examples of suitable forms for administration include injectable preparations of an aqueous, water-miscible or oily nature in which the antibacterial substances in question are dissolved or suspended in the desired concentration. The same also applies to the benzylamine derivatives or the salts thereof, depending on their solubility, while the same preparation may contain one substance in solution and the other in suspension. In those cases where an aqueous solution is desired but is not practicable due to insufficient stability, such as of the antibiotic, the injectable combination is prepared shortly before administration by dissolving or suspending the dry substance in the solvent containing the benzylamine derivative.

The benzylamine derivatives of the formula I and their non-toxic, pharmacologically acceptable acid addition salts are known; see, for example, U.S. Pat. Nos. 3,336,308, 3,536,713 and 4,113,777.

The compounds of the formula I may be obtained in the form of their non-toxic, pharmacologically acceptable acid addition salts after reaction with inorganic or organic acids. Suitable acids include, for example, hydrochloric, hydrobromic, sulfuric, methylsulfuric, phosphoric, tartaric, fumaric, citric, maleic, succinic, gluconic, malic, p-toluenesulfonic, methanesulfonic and amidosulfonic acid.

The following examples illustrate the present invention and will enable others skilled in the art to understand it more completely. It should be understood, however, that the invention is not limited solely to the particular examples given below.

EXAMPLES

EXAMPLE 1

Two-compartment preparation containing 9-deoxy-11-deoxy-9,11-{imino-[2-(2-methoxyethoxy)-ethylidene]-oxy}-(9F)-erythromycin lactobionate (antibiotic) and N-(2-amino-3,5-dibromo-benzyl)-N-methyl-cyclohexylamine hydrochloride (active substance)

| Compostion | |
|---|---|
| (a) Dry ampule | |
| Antibiotic | 715.0 mg |
| (b) Solution ampule | |
| Active substance | 75.0 mg |
| Tartaric acid | 37.5 mg |
| Glycerin polyethyleneglycol oxystearate | 250.0 mg |
| Glucose | 200.0 mg |
| Water for injection q.s. ad | 5.0 ml |

Method

To prepare the dry ampule, the antibiotic is dissolved in water for injection, sterilized, and freed from pyrogens by means of a suitable filter system, possibly by use of pyrogen adsorption layers, and then transferred under aseptic conditions, in the desired dosages, into 10 ml injection vials which have been cleaned and sterilized. These vials are freeze-dried in the usual way.

Next, to prepare the solution ampule, the active substance and excipients are successively dissolved in water for injection purposes, filtering is carried out in the same way as with the dry ampule solution, and the resulting solution is transferred into 5 ml ampules. For sterilization, the fused ampules and the injection vials, sealed with rubber stoppers and crimped aluminum caps, are heated at 121° C. for 20 minutes.

EXAMPLE 2

Two-compartment preparation containing 9-deoxy-11-deoxy-9,11-{imino-[2-(methoxyethoxy)-ethylidene]-oxy}-(9F)-erythromycin lactobionate (antibiotic) and N-(2-amino-3,5-dibromobenzyl)-N-methyl-cyclohexylamine hydrochloride (aqueous solution) (active substance)

| Composition | |
|---|---|
| (a) Dry ampule | |
| Atibiotic | 3575.0 mg |
| (b) Solution ampule | |
| Active substance | 375.0 mg |
| Tartaric acid | 187.5 mg |
| Glycerin polyethyleneglycol oxystearate | 1250.0 mg |
| Glucose | 1250.0 mg |
| Water for injection q.s. ad | 1000.0 mg |
|  | 25.0 ml |

Method

The ampules (a) and (b) are prepared by a procedure analogous to that of Example 1. However, the active substance is transferred into 25 ml or 30 ml injection vials.

EXAMPLE 3

Oily suspension containing 9-deoxy-11-deoxy-9,11-{imino-[-2-(2-methoxyethoxy)-ethylidene]-oxy}-(9F)-erythromycin (antibiotic) and N-(3,5-dibromo-2-hydroxy-benzyl)-trans-4-cyclohexylamine hydrochloride (active substance)

| Composition | |
|---|---|
| Antibiotic | 500.0 mg |
| Active substance | 100.0 mg |
| Benzyl alcohol | 50.0 mg |
| Neutral oil q.s. ad | 5.0 ml |

Method

The antibiotic and active substance are dissolved or suspended in a mixture of the two excipients, while heating, and the resulting mixture is transferred under aseptic conditions into 5 ml-ampules which have been cleaned and sterilized.

EXAMPLE 4

Oily suspension containing 9-deoxy-11-deoxy-9,11-{imino-[2-(2-methoxyethoxy)-ethylidene]-oxy}-(9F)-erythromycin (antibiotic) and N-(3,5-dibromo-2-hydroxy-benzyl)-trans-4-cyclohexylamine hydrochloride (active substance)

| Composition | |
|---|---|
| Antibiotic | 2500.0 mg |
| Active substance | 500.0 mg |
| Benzyl alcohol | 250.0 mg |
| Neutral oil q.s. ad | 25.0 ml |

Method

The antibiotic and the active substance are dissolved or suspended in a mixture of the two excipients, while heating, and the resulting mixture is transferred, under aseptic conditions, into 25 ml injection vials which have been cleaned and sterilized.

EXAMPLE 5

Two-compartment preparation containing 9-deoxy-11-deoxy-9,11-{imino-[2-(2-methoxyethoxy)-ethylidene]-oxy}-(9F)-erythromycin lactobionate (antibiotic) and N-(3,5-dibromo-2-hydroxy-benzyl)-trans-4-hydroxy-cyclohexylamine hydrochloride (aqueous suspension) (active substance)

| Composition | |
|---|---|
| (a) Dry ampule | |
| Antibiotic | 715.0 mg |
| (b) Ampule containing suspension/solution | |
| Active substance | 100.0 mg |
| Polyethyleneglycol stearate | 1.0 mg |
| Sorbitol | 250.0 mg |
| Methyl hydroxyethyl cellulose | 15.0 mg |
| Water for injection q.s. ad | 5.0 ml |

Method

To prepare the dry ampule, the active substance is dissolved in water for injection, sterilized, freed from pyrogens by means of a suitable filter system, possibly by use of pyrogen adsorption layers, and then transferred under aseptic conditions, in the desired dosages, into 10 ml injection vials which have been cleaned and sterilized. These vials are freeze-dried in the usual way.

Next, to prepare the ampules of suspension/solution, the excipients are dissolved in water for injection purposes, and the solution is filtered to sterilize it and to remove any pyrogens. The active substance is suspended in this solution under aseptic conditions, and the suspension is transferred, while stirring, into 5 ml-ampules which have been cleaned and sterilized.

EXAMPLE 6

Two-compartment preparation containing 9-deoxy-11-deoxy-9,11-{imino-[2-(2-methoxyethoxy)-ethylidene]-oxy}-(9F)-erythromycin lactobionate (antibiotic) and N-(3,5-dibromo-2-hydroxy-benzyl)-trans-4-hydroxy-cyclohexylamine hydrochloride (aqueous suspension) (active substance)

| Composition | |
|---|---|
| (a) Dry ampule | |
| Antibiotic | 3575.0 mg |
| (b) Ampule containing suspension/solution | |
| Active substance | 500.0 mg |
| Polyethyleneglycol stearate | 5.0 mg |
| Sorbitol | 1250.0 mg |
| Methyl hydroxyethyl cellulose | 75.0 mg |
| Water for injection q.s. ad | 25.0 ml |

Method

The ampules (a) and (b) are prepared by a procedure analogous to that of Example 5. However, the components are transferred into 25 ml and 30 ml injection vials, respectively.

EXAMPLE 7

Injectable solution containing oxytetracycline hydrochloride (antibiotic) and N-(3,5-dibromo-2-hydroxy-benzyl)-trans-4-hydroxy-cyclohexylamine (active substance)

| Composition | |
|---|---|
| Antibiotic | 5.0 gm |
| Active substance | 0.05–0.8 gm |
| Magnesium oxide | 0.45 gm |
| pH adjuster | 1.0 gm |
| Antioxidants | 0.2 gm |
| Solketal ® | 15.0 gm |
| 1,2-Propyleneglycol | 74.0 gm |
| Water for injection q.s. ad | 100.0 ml |

Method

In a suitable vessel, the antibiotic is dissolved in the corresponding quantity of water, and 1,2-propyleneglycol and then magnesium oxide are added. At the same time, a solution of Solketal ® and active substance in the corresponding quantity of 1,2-propyleneglycol is prepared. The two solutions are combined, and a solution of the antioxidants in a small amount of water is added thereto. The desired pH value is obtained by adding the pH adjuster. The solution is prepared and transferred into vials in a nitrogen atmosphere and under aseptic conditions. The solution must be sterilized by filtration.

EXAMPLE 8

Aqueous suspension containing chloramphenicol or thiamphenicol (antibiotic) and N-(3,5-dibromo-2-hydroxy-benzyl)-trans-4-hydroxy-cyclohexylamine hydrochloride (active substance)

| Composition | |
|---|---|
| Antibiotic | 20.0 gm |
| Active substance | 0.05–2.5 gm |
| Suspension stabilizers | 1.6 gm |
| Emulsifier | 2.0 gm |
| Citric acid | 1.0 gm |
| Antifoaming agent | 0.2 gm |
| Methiolate | 0.005 gm |
| 1 N Sodium hydroxide solution | 3.25 gm |
| Water for injection q.s. ad | 100.0 ml |

Method

Merthiolate and citric acid are dissolved in about one-third of the quantity of water and placed in a suitable vessel. The active substance, suspension stabilizers, and antifoaming agent are successively added to this solution and dissolved or suspended therein.

The emulsifier is dissolved in about one-third of the quantity of water, while heating, and added thereto. A suspension of antibiotic in water is added, with stirring, while the homogeneous suspension is adjusted to the desired pH value with 1N NaOH, having been diluted to 100 ml with the remaining water. All the excipients and active substances or solutions thereof are sterilized before use. The preparation must be made up and bottled under aseptic conditions.

EXAMPLE 9

Injection solution containing tylosin and N-(2-amino-3,5-dibromobenzyl)-N-methyl-cyclohexylamine hydrochloride (active substance)

| Composition | |
|---|---|
| Tylosin | 50.0 mg |
| Active substance | 0.5–6.0 mg |
| 1,2-Propyleneglycol | 0.5 ml |
| Benzyl alcohol | 0.04 ml |
| Hydrochloric acid q.s. ad | pH 4 |
| Water for injection q.s. ad | 1.0 ml |

Method

The active substance is dissolved in 90 ml of a suitable mixture of 1,2-propyleneglycol and water, with stirring and ultrasonic treatment, in a current of nitrogen. Tylosin is added and dissolved to form a clear solution. After the addition of the benzyl alcohol, the mixture is adjusted to the desired pH with 1N HCl and then diluted to 100 ml with water. The solution must be prepared and bottled under aseptic conditions.

EXAMPLE 10

Injection solution containing tylosin and N-(3,5-dibromo-2-hydroxy-benzyl)-trans-4-hydroxy-cyclohexylamine hydrochloride (active substance)

| Composition | |
|---|---|
| Tylosin | 50.0 mg |
| Active substance | 0.5–6.0 mg |
| 1,2-Propyleneglycol | 0.5 ml |
| Benzyl alcohol | 0.04 ml |
| Hydrochloric acid q.s. ad | pH 4 |
| Water for injection q.s. ad | 1.0 ml |

Method

The solution is prepared by using a procedure analogous to that of Example 9.

EXAMPLE 11

Oil suspension containing erythromycin and N-(3,5-dibromo-2-hydroxy-benzyl)-trans-4-hydroxy-cyclohexylamine hydrochloride (active substance)

| Composition | |
|---|---|
| Erythromycin | 50.0 mg |
| Active substance | 0.5–25.0 mg |
| Sodium diotylsulfosuccinate | 2.0 mg |
| Neutral oil q.s. ad | 1.0 ml |

Method

Sodium dioctylsulfosuccinate is dissolved in the corresponding quantity of neutral oil while heating and stirring. After the solution has cooled to room temperature, erythromycin is dissolved therein, and active substance of a suitable particle size is added. The resulting suspension is homogenized with a suitable stirrer and bottled under aseptic conditions.

EXAMPLE 12

Suspension containing erythromycin and N-(2-amino-3,5-dibromo-benzyl)-N-methyl-cyclohexylamine (active substance)

| Composition | |
|---|---|
| Erythromycin | 50.0 mg |
| Active substance | 0.5–25.0 mg |
| Neutral oil | q.s. ad 1.0 ml |

Method

The suspension is prepared using a procedure analogous to that of Example 11.

EXAMPLE 13

Injection solution containing trimethoprim, sulfadimidine, sulfathiazole, and N-(2-amino-3,5-dibromo-benzyl)-N-methyl-cyclohexylamine hydrochloride (active substance)

| Composition | |
|---|---|
| Trimethoprim | 40.0 mg |
| Sulfadimidine | 100.0 mg |
| Sulfathiazole | 100.0 mg |
| Active substance | 0.5–6.0 mg |
| Glycerol formal | q.s. ad 1.0 ml |

Method

The active substance is dissolved in glycerol formal while stirring and in a current of nitrogen. Then, trimethoprim, sulfadimidine and sulfathiazole are successively dissolved therein, while stirring. The solution is then diluted with the remaining glycerol formal. The preparation must be made up and bottled under aseptic conditions and in the absence of direct light.

EXAMPLE 14

Injection solution containing trimethoprim, sulfadimidine, sulfathiazole and N-(3,5-dibromo-2-hydroxy-benzyl)-trans-4-hydroxy-cyclohexylamine hydrochloride (active substance)

| Composition | |
|---|---|
| Trimethoprim | 40.0 mg |
| Sulfadimidine | 100.0 mg |
| Sulfathiazole | 100.0 mg |
| Active substance | 0.5–15.0 mg |
| Glycerin formal | q.s. ad 1.0 ml |

Method

The solution is prepared by using a procedure analogous to that of Example 13.

EXAMPLE 15

Injection solution containing spiramycin and N-(2-amino-3,5-dibromo-benzyl)-trans-4-hydroxy-cyclohexylamine hydrochloride (active substance)

| Composition | |
|---|---|
| Active substance | 0.5–6.0 mg |
| Spiramycin | 50.0 mg |

-continued

| Composition | |
|---|---|
| 1,2-Propyleneglycol | 0.5 ml |
| Water for injection | q.s. ad 1.0 ml |
| 1 N Hydrochloric acid | q.s. ad pH 3.8 |

Method

The active substance is dissolved, while stirring, in a mixture of 1,2-propyleneglycol and water in a current of nitrogen, and the spiramycin is dissolved in the solution. The solution is adjusted to the desired pH with 1N HCl and diluted with water. The preparation must be made up and bottled under aseptic conditions.

EXAMPLE 16

Injection solution containing spiramycin and N-(3,5-dibromo-2-hydroxy-benzyl)-trans-4-hydroxy-cyclohexylamine

| Composition | |
|---|---|
| Active substance | 0.5–15.0 mg |
| Spiramycin | 50.0 mg |
| Glycofurol | q.s. ad 1.0 ml |

Method

A solution of spiramycin in glycofurol is prepared in a current of nitrogen and then the active substance is added to the solution in small portions, again in a current of nitrogen, and dissolved therein. The solution is bottled under aseptic conditions and in an atmosphere of nitrogen.

EXAMPLE 17

Two-compartment preparation containing 9-deoxy-11-deoxy-9,11-{imino-[2-(2-methoxyethoxy)-ethylidene]-oxy}-(9F)-erythromycin lactobionate (antibiotic) and N-(2-amino-3,5-dibromo-benzyl)-trans-4-hydroxy-cyclohexylamine hydrochloride (active substance)

| Composition | |
|---|---|
| (a) Dry ampule. | |
| Antibiotic | 715.0 mg |
| (b) Solution ampule. | |
| Active substance | 75.0 mg |
| Tartaric acid | 37.5 mg |
| Glycerin polyethyleneglycol oxystearate | 250.0 mg |
| Glucose | 200.0 mg |
| Water for injection | q.s. ad 5.0 ml |

Method

The ampules (a) and (b) are prepared by a procedure analogous to that of Example 1.

EXAMPLE 18

Oily suspension containing 9-deoxy-11-deoxy-9,11-{imino-[2-(2-methoxyethoxy)-ethylidene]-oxy}-(9F)-erythromycin (antibiotic) and N-(2-amino-3,5-dibromo-benzyl)-N-methyl-cyclohexylamine hydrochloride (active substance)

| Composition | |
|---|---|
| Antibiotic | 200.0 mg |
| Active substance | 2.0–20.0 mg |
| 4-Chloro-m-cresol | 2.0 mg |
| Aluminum monostearate | 10.0 mg |
| Neutral oil (e.g. Miglyol ® 812 available from Dynamit Nobel Co.) | q.s. ad 1.0 ml |

Preparation

The aluminum monostearate is dispersed in the corresponding quantity of neutral oil, while stirring and heating. After the mixture has cooled to room temperature, first the 4-Chloro-m-cresol, then the antibiotic and the active substance in a suitable particle size are added and dissolved or suspended while stirring. The resulting suspension is filled into ampules under aseptic conditions.

EXAMPLE 19

Oily suspension containing 9-deoxy-11-deoxy-9,11-{imino-[2-(2-methoxyethoxy)-ethylidene]-oxy}-(9F)-erythromycin lactobionate (antibiotic) and N-(2-amino-3,5-dibromo-benzyl)-N-methyl-cyclohexylamine hydrochloride (active substance)

| Composition | |
|---|---|
| Antibiotic | 285.8 mg |
| Active substance | 2.0–20.0 mg |
| 4-Chloro-m-cresol | 2.0 mg |
| Aluminum monostearate | 10.0 mg |
| Neutral oil (e.g. Miglyol ® 812) | q.s. ad 1.0 ml |

Preparation

Analogous to Example 18.

EXAMPLE 20

Oily suspension containing 9-deoxy-11-deoxy-9,11-{imino-[2-(2-methoxyethoxy)-ethylidene]-oxy}-(9F)-erythromycin lactobionate (antibiotic) and N-(2-amino-3,5-dibromo-benzyl)-N-methyl-cyclohexylamine hydrochloride (active substance)

| Composition | |
|---|---|
| Antibiotic | 143.0 mg |
| Active substance | 2.0–20.0 mg |
| 4-Chloro-m-cresol | 2.0 mg |
| Aluminum monostearate | 10.0 mg |
| Neutral oil (e.g. Miglyol ® 812) | q.s. ad 1.0 ml |

Preparation

Analogous to Example 18.

EXAMPLE 21

Oily suspension containing
9-deoxy-11-deoxy-9,11-{imino-[2-(2-methoxyethoxy)-ethylidene]-oxy}-(9F)-erythromycin (antibiotic) and
N-(2-amino-3,5-dibromo-benzyle-N-methyl-cyclohexylamine hydrochloride (active substance)

| Composition | |
|---|---|
| Antibiotic | 100.0 mg |
| Active substance | 2.0–20.0 mg |
| 4-Chloro-m-cresol | 2.0 mg |
| Aluminum monostearate | 10.0 mg |
| Neutral oil (e.g. Miglyol ® 812) | q.s. ad 1.0 ml |

Preparation

Analogous to Example 18.

EXAMPLE 22

Oily suspension containing
9-deoxy-11-deoxy-9,11-{imino-[2-(2-methoxyethoxy)-ethylidene]-oxy}-(9F)-erythromycin (antibiotic) and
N-(3,5-dibromo-2-hydroxy-benzyl)-trans-4-hydroxy-cyclohexylamine hydrochloride (active substance)

| Composition | |
|---|---|
| Antibiotic | 200.0 mg |
| Active substance | 3.0–20.0 mg |
| 4-Chloro-m-cresol | 2.0 mg |
| Aluminum monostearate | 10.0 mg |
| Neutral oil (e.g. Miglyol ® 812) | q.s. ad 1.0 ml |

Preparation

Analogous to Example 18.

EXAMPLE 23

Oily suspension containing
9-deoxy-11-deoxy-9,11-{imino-[2-(2-methoxyethoxy)-ethylidene]-oxy}-(9F)-erythromycin lactobionate (antibiotic) and
N-(3,5-dibromo-2-hydroxy-benzyl)-trans-4-hydroxy-cyclohexylamine hydrochloride (active substance)

| Composition | |
|---|---|
| Antibiotic | 285.8 mg |
| Active substance | 3.0–20.0 mg |
| 4-Chloro-m-cresol | 2.0 mg |
| Aluminum monostearate | 10.0 mg |
| Neutral oil (e.g. Miglyol ® 812) | q.s. ad 1.0 ml |

Preparation

Analogous to Example 18.

EXAMPLE 24

Oily suspension containing
9-deoxy-11-deoxy-9,11-{imino-[2-(2-methoxyethoxy)-ethylidene]-oxy}-(9F)-erythromycin lactobionate (antibiotic) and
N-(3,5-dibromo-2-hydroxy-benzyl)-trans-4-hydroxy-cyclohexylamine hydrochloride (active substance)

| Composition | |
|---|---|
| Antibiotic | 143.0 mg |
| Active substance | 3.0–20.0 mg |
| 4-Chloro-m-cresol | 2.0 mg |
| Aluminum monostearate | 10.0 mg |
| Neutral oil (e.g. Miglyol ® 812) | q.s. ad 1.0 ml |

Preparation

Analogous to Example 18.

EXAMPLE 25

Oily suspension containing
9-deoxy-11-deoxy-9,11-{imino-[2-(2-methoxyethoxy)-ethylidene]-oxy}-(9F)-erythromycin (antibiotic) and
N-(3,5-dibromo-2-hydroxy-benzyl)-trans-4-hydroxy-cyclohexylamine hydrochloride (active substance)

| Composition | |
|---|---|
| Antibiotic | 100.0 mg |
| Active substance | 3.0–20.0 mg |
| 4-Chloro-m-cresol | 2.0 mg |
| Aluminum monostearate | 10.0 mg |
| Neutral oil (e.g. Miglyol ® 812) | q.s. ad 1.0 ml |

Preparation

Analogous to Example 18.

EXAMPLE 26

Oily suspension containing oxytetracyclin hydrochloride (antibiotic) and
N-(2-amino-3,5-dibromo-benzyl)-N-methyl-cyclohexylamine hydrochloride (active substance)

| Composition | |
|---|---|
| Antibiotic | 200.0 mg |
| Active substance | 2.0–20.0 mg |
| 4-Chloro-m-cresol | 2.0 mg |
| Sodium dioctylsulfosuccinate | 0.7 mg |
| Neutral oil (e.g. Miglyol ® 812) | q.s. ad 1.0 ml |

Preparation

Production takes place under aseptic conditions and constant gas load. Sodium dioctylsulfosuccinate and 4-Chloro-m-cresol are dissolved in a suitable quantity of neutral oil while stirring. The solution is sterilized by filtration. Oxytetracyclin x HCl and the active substance are added to another suitable quantity of neutral oil while stirring, and the resulting suspension is milled to micronize the antibiotic particles. Solution and suspension are then combined, homogenized and filled into ampules under sterile conditions.

EXAMPLE 27

Oily suspension containing oxytetracyclin hydrochloride (antibiotic) and N-(3,5-dibromo-2-hydroxy-benzyl)-trans-4-hydroxy-cyclohexylamine hydrochloride (active substance)

| Composition | |
|---|---|
| Antibiotic | 200.0 mg |
| Active substance | 3.0–20.0 mg |
| 4-Chloro-m-cresol | 2.0 mg |
| Sodium dioctylsulfosuccinate | 0.7 mg |
| Neutral oil (e.g. Miglyol ® 812) q.s. ad | 1.0 ml |

Preparation

Analogous to Example 26.

EXAMPLE 28

Sterile solid for injection containing ampicillin and N-(2-amino-3,5-dibromo-benzyl)-N-methyl-cyclohexylamine hydrochloride (active substance)

| Composition | |
|---|---|
| Ampicillin × 3 H$_2$O | 173.0 mg |
| Active substance | 4.0–40.0 mg |

Solvent ampule

| Composition | |
|---|---|
| Tartaric acid | 2.0–8.0 mg |
| Sodium hydroxide | 0.5 mg |
| Polyoxyethylene hydrogenated castor oil | 20.0 mg |
| Distilled water q.s. ad | 1.0 ml |

Preparation

The antibiotic and the active substance are filled under sterile conditions into injection vials which then are sealed with a pierceable rubber closure and aluminum cap.

The solvent is prepared in an appropriate volume by dissolving first polyoxyethylene hydrogenated castor oil, while stirring, in a suitable amount of WfI (water for injection), then adding sodium hydroxide and tartaric acid. After adjustment of total volume with WfI, the solution is filtered and filled into ampules. The ampules are sealed and sterilized in an autoclave.

EXAMPLE 29

Sterile solid for injection containing ampicillin and N-(2-amino-3,5-dibromo-benzyl)-N-methyl-cyclohexylamine hydrochloride (active substance)

| Composition | |
|---|---|
| Ampicillin × 3 H$_2$O | 1,730.0 mg |
| Active substance | 40–400.0 mg |

Solvent ampules

| Composition | |
|---|---|
| Tartaric acid | 20.0–80.0 mg |
| Sodium hydroxide | 5.0 mg |
| Polyoxyethylene hydrogenated castor oil | 200.0 mg |
| 4-Chloro-m-cresol | 20.0 mg |
| Distilled water q.s. ad | 10.0 ml |

Preparation

Analogous to Example 28.

EXAMPLE 30

Oily suspension containing ampicillin and N-(2-amino-3,5-dibromo-benzyl)-N-methyl-cyclohexylamine hydrochloride (active substance)

| Composition | |
|---|---|
| Ampicillin × 3 H$_2$O | 173.0 mg |
| Active substance | 4.0–40.0 mg |
| 4-Chloro-m-cresol | 2.0 mg |
| Sodium dioctylsulfosuccinate | 0.7 mg |
| Neutral oil (e.g. Miglyol ® 812) q.s. ad | 1.0 ml |

Preparation

Analogous to Example 26.

EXAMPLE 31

Sterile solid for injection containing ampicillin and N-(2-amino-3,5-dibromo-benzyl)-N-methyl-cyclohexylamine hydrochloride (active substance)

| Composition | |
|---|---|
| Ampicillin × 3 H$_2$O | 230.0 mg |
| Active substance | 4.0–40.0 mg |

Solvent ampule

| Composition | |
|---|---|
| Tartaric acid | 2.0–8.0 mg |
| Sodium hydroxide | 0.5 mg |
| Polyoxyethylene hydrogenated castor oil | 20.0 mg |
| Distilled water q.s. ad | 1.0 ml |

Preparation

Analogous to Example 28.

EXAMPLE 32

Oily suspension containing ampicillin and N-(2-amino-3,5-dibromo-benzyl)-N-methyl-cyclohexylamine hydrochloride (active substance)

| Composition | |
|---|---|
| Ampicillin × 3 H$_2$O | 230.0 mg |
| Active substance | 4.0–40.0 mg |
| 4-Chloro-m-cresol | 2.0 mg |
| Sodium dioctylsulfosuccinate | 1.0 mg |
| Neutral oil (e.g. Miglyol ® 812) q.s. ad | 1.0 ml |

Preparation

Analogous to Example 26.

EXAMPLE 33

Sterile solid for injection containing benzathine ampicillin and
N-(2-amino-3,5-dibromo-benzyl)-N-methyl-cyclohexylamine hydrochloride (active substance)

| Composition | |
|---|---|
| Benzathine ampicillin | 276.5 mg |
| Active substance | 4.0–40.0 mg |

Solvent ampule

| Composition | |
|---|---|
| Tartaric acid | 2.0–8.0 mg |
| Sodium hydroxide | 0.5 mg |
| Polyoxyethylene hydrogenated castor oil | 30.0 mg |
| Distilled water q.s. ad | 1.0 ml |

Preparation

Analogous to Example 28.

EXAMPLE 34

Oily suspension containing benzathine ampicillin, ampicillin sodium and
N-(2-amino-3,5-dibromo-benzyl)-N-methyl-cyclohexylamine hydrochloride (active substance)

| Composition | |
|---|---|
| Benzathine ampicillin | 276.5 mg |
| Ampicillin sodium | 21.3 mg |
| Active substance | 4.0–40.0 mg |
| 4-Chloro-m-cresol | 2.0 mg |
| Sodium dioctylsulfosuccinate | 1.5 mg |
| Neutral oil (e.g. Miglyol ® 812) q.s. ad | 1.0 ml |

Preparation

Analogous to Example 26.

EXAMPLE 35

Sterile solid for injection containing ampicillin and
N-(3,5-dibromo-2-hydroxy-benzyl)-trans-4-hydroxy-cyclohexylamine hydrochloride (active substance)

| Composition | |
|---|---|
| Ampicillin × 3 H$_2$O | 173.0 mg |
| Active substance | 6.0–24.0 mg |

Solvent ampule

| Composition | |
|---|---|
| Tartaric acid | 2.0–8.0 mg |
| Sodium hydroxide | 0.5 mg |
| Polyoxyethylene hydrogenated castor oil | 20.0 mg |
| Distilled water | q.s. ad 1.0 ml |

Preparation

Analogous to Example 28.

EXAMPLE 36

Oily suspension containing ampicillin and
N-(3,5-dibromo-2-hydroxy-benzyl)-trans-4-hydroxy-cyclohexylamine hydrochloride (active substance)

| Composition | |
|---|---|
| Ampicillin × 3 H$_2$O | 173.0 mg |
| Active substance | 6.0–24.0 mg |
| 4-Chloro-m-cresol | 2.0 mg |
| Sodium dioctylsulfosuccinate | 0.7 mg |
| Neutral oil (e.g. Miglyol ® 812) | q.s. ad 1.0 ml |

Preparation

Analogous to Example 26.

EXAMPLE 37

Sterile solid for injection containing ampicillin and
N-(3,5-dibromo-2-hydroxy-benzyl)-trans-4-hydroxy-cyclohexylamine hydrochloride (active substance)

| Composition | |
|---|---|
| Ampicillin × 3 H$_2$O | 230.0 mg |
| Active substance | 6.0–4.0 mg |

Solvent ampule

| Composition | |
|---|---|
| Tartaric acid | 2.0–8.0 mg |
| Sodium hydroxide | 0.5 mg |
| Polyoxyethylene hydrogenated castor oil | 20.0 mg |
| Distilled water | q.s. ad 1.0 ml |

Preparation

Analogous to Example 28.

EXAMPLE 38

Oily suspension containing ampicillin and
N-(3,5-dibromo-2-hydroxy-benzyl)-trans-4-hydroxy-cyclohexylamine hydrochloride (active substance)

| Composition | |
|---|---|
| Ampicillin × 3 H$_2$O | 230.0 mg |
| Active substance | 6.0–24.0 mg |
| 4-Chloro-m-cresol | 2.0 mg |
| Sodium dioctylsulfosuccinate | 1.0 mg |
| Neutral oil (e.g. Miglyol ® 812) | q.s. ad 1.0 ml |

Preparation

Analogous to Example 26.

EXAMPLE 39

Sterile solid for injection containing benzathine ampicillin and
N-(3,5-dibromo-2-hydroxy-benzyl)-trans-4-hydroxy-cyclohexylamine hydrochloride (active substance)

| Composition | |
|---|---|
| Benzathine ampicillin | 276.5 mg |
| Active substance | 6.0–24.0 mg |

Solvent ampule

| Composition | |
|---|---|
| Tartaric acid | 2.0–8.0 mg |
| Sodium hydroxide | 0.5 mg |
| Polyoxyethylene hydrogenated castor oil | 30.0 mg |
| Distilled water | q.s. ad 1.0 ml |

Preparation

Analogous to Example 28.

EXAMPLE 40

Oily suspension containing benzathine ampicillin, ampicillin sodium and N-(3,5-dibromo-2-hydroxy-benzyl)-trans-4-hydroxy-cyclohexylamine hydrochloride (active substance)

| Composition | |
|---|---|
| Benzathine ampicillin | 276.5 mg |
| Ampicillin sodium | 21.3 mg |
| Active substance | 6.0–24.0 mg |
| 4-Chloro-m-cresol | 2.0 mg |
| Sodium dioctylsulfosuccinate | 1.5 mg |
| Neutral oil (e.g. Miglyol ® 812) | q.s. ad 1.0 ml |

Preparation

Analogous to Example 26.

EXAMPLE 41

Sterile solid for injection containing ampicillin and N-(3,5-dibromo-2-hydroxy-benzyl)-trans-4-hydroxy-cyclohexylamine hydrochloride (active substance)

| Composition | |
|---|---|
| Ampicillin × 3 H$_2$O | 173.0 mg |
| Active substance | 6.0–40.0 mg |

Solvent ampule

| Composition | |
|---|---|
| Tartaric acid | 2.0–8.0 mg |
| Sodium hydroxide | 0.5 mg |
| Polyoxyethylene hydrogenated castor oil | 20.0 mg |
| Distilled water | q.s. ad 1.0 ml |

Preparation

Analogous to Example 28.

EXAMPLE 42

Oily suspension containing ampicillin and N-(3,5-dibromo-2-hydroxy-benzyl)-trans-4-hydroxy-cyclohexylamine hydrochloride (active substance)

| Composition | |
|---|---|
| Ampicillin × 3 H$_2$O | 173.0 mg |
| Active substance | 6.0–40.0 mg |
| 4-Chloro-m-cresol | 2.0 mg |
| Sodium dioctylsulfosuccinate | 0.7 mg |
| Neutral oil (e.g. Miglyol ® 812) | q.s. ad 1.0 ml |

Preparation

Analogous to Example 26.

EXAMPLE 43

Sterile solid for injection containing ampicillin and N-(3,5-dibromo-2-hydroxy-benzyl)-trans-4-hydroxy-cyclohexylamine hydrochloride (active substance)

| Composition | |
|---|---|
| Ampicillin × 3 H$_2$O | 230.0 mg |
| Active substance | 6.0–40.0 mg |

Solvent ampule

| Composition | |
|---|---|
| Tartaric acid | 2.0–8.0 mg |
| Sodium hycroxide | 0.5 mg |
| Polyoxyethylene hydrogenated castor oil | 20.0 mg |
| Distilled water | q.s. ad 1.0 ml |

Preparation

Analogous to Example 28.

EXAMPLE 44

Oily suspension containing ampicillin and N-(3,5-dibromo-2-hydroxy-benzyl)-trans-4-hydroxy-cyclohexylamine hydrochloride

| Composition | |
|---|---|
| Ampicillin × 3 H$_2$O | 230.0 mg |
| Active substance | 6.0–40.0 mg |
| 4-Chloro-m-cresol | 2.0 mg |
| Sodium dioctylsulfosuccinate | 1.0 mg |
| Neutal oil (e.g. Miglyol ® 812) | q.s. ad 1.0 ml |

Preparation

Analogous to Example 26.

EXAMPLE 45

Sterile solid for injection containing benzathine ampicillin and N-(3,5-dibromo-2-hydroxy-benzyl)-trans-4-hydroxy-cyclohexylamine hydrochloride (active substance)

| Composition | |
|---|---|
| Benzathine ampicillin | 276.5 mg |
| Active substance | 6.0–40.0 mg |

Solvent ampule

| Composition | |
|---|---|
| Tartaric acid | 2.0–8.0 mg |
| Sodium hydroxide | 0.5 mg |
| Polyoxyethylene hydrogenated castor oil | 30.0 mg |
| Distilled water q.s. ad | 1.0 ml |

Preparation

Analogous to Example 28.

EXAMPLE 46

Oily suspension containing benzathine ampicillin, ampicillin sodium and N-(3,5-dibromo-2-hydroxy-benzyl)-trans-4-hydroxy-cyclohexylamine hydrochloride (active substance)

| Composition | |
| --- | --- |
| Benzathine ampicillin | 276.5 mg |
| Ampicillin sodium | 21.3 mg |
| Active substance | 6.0–40.0 mg |
| 4-Chloro-m-cresol | 2.0 mg |
| Sodium dioctylsulfosuccinate | 1.5 mg |
| Neutral oil (e.g. Miglyol ® 812) q.s. ad | 1.0 ml |

Preparation

Analogous to Example 26.

Any one of the other compounds embraced by formula I or a non-toxic, pharmacologically acceptable acid addition salt thereof may be substituted for the particular active substance in Examples 18 through 46. Likewise, the amount of antibiotic and active substance in these illustrative examples may be varied to achieve the dosage ranges set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of increasing the absorption of a parenterally administered delayed-release oxytetracycline or delayed-release oxytetracycline hydrochloride in an animal host, which comprises parenterally administering to said host (a) N-(2-amino-3,5-dibromo-benzyl)-N-methyl-cyclohexylamine or a non-toxic, pharmacologically acceptable acid addition salt thereof, and (b) an effective antibacterial amount of a delayed-release oxytetracycline or a delayed-release oxytetracycline hydrochloride.

* * * * *

UNITED STATES PATENT AND TRADEMARK OFFICE
CERTIFICATE OF CORRECTION

PATENT NO. : 4,918,108

DATED : April 17, 1990

INVENTOR(S) : Otto Kern et al

It is certified that error appears in the above-identified patent and that said Letters Patent is hereby corrected as shown below:

Column 8, line 63 should read --Neutral oil............q.s. ad 250.0 ml-- (250.0 ml should aligned under 250.0 mg).

Column 20, line 26, "6.0-4.0 mg" should read --6.0-24.0 mg--.

Column 22, line 21, "hycroxide" should read --hydroxide--.

Signed and Sealed this

Second Day of February, 1993

Attest:

STEPHEN G. KUNIN

*Attesting Officer*  *Acting Commissioner of Patents and Trademarks*